US00PP30257P2

(12) United States Plant Patent
Holtmaat

(10) Patent No.: US PP30,257 P2
(45) Date of Patent: Feb. 26, 2019

(54) ***MONARDA* PLANT NAMED 'MONARD0039'**

(50) Latin Name: *Monarda didyma*
Varietal Denomination: MONARD0039

(71) Applicant: Henricus Maria Joseph Holtmaat, Zuidwolde (NL)

(72) Inventor: Henricus Maria Joseph Holtmaat, Zuidwolde (NL)

(73) Assignee: AB Kwekersrechten B.V., Zuidwolde (NL)

( * ) Notice: Subject to any disclaimer, the term of this patent is extended or adjusted under 35 U.S.C. 154(b) by 0 days.

(21) Appl. No.: 15/732,923

(22) Filed: Jan. 13, 2018

(51) Int. Cl.
*A01H 5/02* (2018.01)

(52) U.S. Cl.
USPC ..... Plt./455
CPC ..... *A01H 5/02* (2013.01)

(58) Field of Classification Search
USPC ..... Plt./455
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Monarda* plant named 'MONARD0039', characterized by its broadly upright plant habit; dark green-colored leaves; freely flowering habit; large inflorescences with purple-colored flowers; long flowering period; and tolerance to Powdery Mildew.

2 Drawing Sheets

Botanical designation: *Monarda didyma.*
Cultivar denomination: 'MONARD0039'.

CROSS-REFERENCED TO CLOSELY-RELATED APPLICATIONS

Title: *Monarda* Plant Named 'MONARD0044'
Applicant: Henricus Maria Joseph Holtmaat
Filed: Concurrently with this application, Ser. No. 15/732,917

BACKGROUND OF THE INVENTION

The present invention relates to a new and distinct cultivar of *Monarda* plant, botanically known as *Monarda didyma*, typically grown as a container plant and hereinafter referred to by the name 'MONARD0039'.

The new *Monarda* plant is a product of a planned breeding program conducted by the Inventor in Zuidwolde, The Netherlands. The objective of the breeding program is to create new *Monarda* plants with attractive flowers and tolerance to Powdery Mildew.

The new *Monarda* plant originated from a cross-pollination in July, 2014 of two unnamed selections of *Monarda didyma*, not patented. The new *Monarda* plant was discovered and selected by the Inventor as a single flowering plant from within the progeny of the stated cross-pollination grown in a controlled environment in Zuidwolde, The Netherlands in July, 2016.

Asexual reproduction of the new *Monarda* plant by vegetative terminal cuttings in Zuidwolde, The Netherlands, since March, 2017 has shown that the unique features of this new *Monarda* plant are stable and reproduced true to type in successive generations.

SUMMARY OF THE INVENTION

Plants of the new *Monarda* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MONARD0039'. These characteristics in combination distinguish 'MONARD0039' as a new and distinct *Monarda* plant:

1. Broadly upright plant habit.
2. Dark green-colored leaves.
3. Freely flowering habit.
4. Large inflorescences with purple-colored flowers.
5. Long flowering period.
6. Tolerant to Powdery Mildew.

Plants of the new *Monarda* differ primarily from plants of the parent selections in plant uniformity as plants of the new *Monarda* are more uniform than plants of the parent selections.

Plants of the new *Monarda* can be compared to plants of *Monarda didyma* 'MONARD0044', disclosed in U.S. Plant Patent filed concurrently, Ser. No. 15/732,917. In side-by-side comparisons, plants of the new *Monarda* differ primarily from plants of 'MONARD0044' in flower color as plants of 'MONARD0044' have purple violet-colored flowers. In addition, plants of the new *Monarda* are larger than plants of 'MONARD0044'.

Plants of the new *Monarda* can be compared to plants of *Monarda didyma* 'Purple Ann', not patented. In side-by-side comparisons, plants of the new *Monarda* differ primarily from plants of 'Purple Ann' in the following characteristics:

1. Plants of the new *Monarda* are more freely flowering than plants of 'Purple Ann'.
2. Plants of the new *Monarda* are more tolerant to Powdery Mildew than plants of 'Purple Ann'.

BRIEF DESCRIPTION OF THE PHOTOGRAPHS

The accompanying colored photographs illustrate the overall appearance of the new *Monarda* plant showing the colors as true as it is reasonably possible to obtain in colored reproductions of this type. Colors in the photographs may differ slightly from the color values cited in the detailed botanical description which accurately describe the actual colors of the new *Monarda* plant.

The photograph on the first sheet is a side perspective view of a typical flowering plant of 'MONARD0039' grown in a container.

The photograph at the top of the second sheet is a close-up view of typical inflorescences of 'MONARD0039'.

The photograph at the bottom of the second sheet is a close-up view of typical leaves of 'MONARD0039'.

DETAILED BOTANICAL DESCRIPTION

The aforementioned photographs and following observations, measurements and values describe plants grown during the late summer and early autumn in 19-cm containers in an outdoor nursery in Zuidwolde, The Netherlands and under cultural practices typical of commercial *Monarda* production. During the production of the plants, day temperatures ranged from 18° C. to 30° C. and night temperatures ranged from 6° C. to 18° C. Plants were one year old when the photographs and the description were taken. In the detailed description, color references are made to The Royal Horticultural Society Colour Chart, 2015 Edition, except where general terms of ordinary dictionary significance are used.

Botanical classification: *Monarda didyma* 'MONARD0039'.

Parentage:

*Female, or seed, parent*.—Unnamed selection of *Monarda didyma*, not patented.

*Male, or pollen, parent*.—Unnamed selection of *Monarda didyma*, not patented.

Propagation:

*Type cutting*.—By terminal vegetative cuttings.

*Time to initiate roots, summer*.—About 15 days at temperatures about 20° C.

*Time to produce a rooted young plant, summer*.—About two months at temperatures about 20° C.

*Root description*.—Medium in thickness, fibrous; typically creamy white in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Herbaceous perennial; broadly upright plant habit; overall plant form, obovate; moderately vigorous growth habit; moderate growth rate.

*Plant height, soil level to top of foliar plane*.—About 52.6 cm.

*Plant height, soil level to top of floral plane*.—About 57.8 cm.

*Plant width*.—About 57 cm.

*Lateral branch description*.—Branching habit: Freely basal branching habit with about 33 main stems. Length: About 13.8 cm. Diameter: About 3.5 mm. Internode length: About 4.8 cm. Strength: Strong. Aspect: About 20° to 50° from vertical. Texture and luster: Moderately pubescent; slightly glossy. Color, developing: Close to 144B. Color, developed: Close to 144A.

Leaf description:

*Arrangement*.—Opposite, simple.

*Length*.—About 10.2 cm.

*Width*.—About 6 cm.

*Shape*.—Ovate.

*Apex*.—Apiculate.

*Base*.—Truncate.

*Margin*.—Serrate.

*Texture and luster, upper surface*.—Moderately pubescent and slightly rugose; slightly glossy.

*Texture and luster, lower surface*.—Densely pubescent and moderately rugose; matted.

*Venation pattern*.—Pinnate.

*Fragrance*.—Moderately fragrant; pleasant, spicy.

*Color*.—Developing leaves, upper surface: Close to 137B. Developing leaves, lower surface: Close to 138B. Fully expanded leaves, upper surface: Slightly darker than between NN137A and 147A; venation, close to 146C. Fully expanded leaves, lower surface: Close to between 137B and 147B; venation, close to 146D.

*Petioles*.—Length: About 1.6 cm. Diameter: About 2 mm by 3 mm. Strength: Strong. Texture, upper surface: Smooth, glabrous; slightly glossy. Texture, lower surface: Densely pubescent; matte. Color, upper surface: Close to 144C. Color, lower surface: Close to 144B.

Flower description:

*Flower form, arrangement and flowering habit*.—Single labiate flowers arranged in large terminal globular spikes; flowers sessile; flowers face upright to outwardly; freely flowering habit with about 200 flowers developing per inflorescence and about 14,000 flowers developing per plant during the flowering season.

*Natural flowering season*.—Long flowering habit, plants flower from late spring into the summer in The Netherlands; plants begin flowering about two months after planting.

*Postproduction longevity*.—Flowers maintain good substance for about one week on the plant; flowers not persistent.

*Fragrance*.—None detected.

*Flower buds*.—Length: About 2.7 cm. Diameter: About 5 mm. Shape: Narrowly oblanceolate; curved. Texture and luster: Densely pubescent; matte. Color: Close to 77A to slightly darker than 77A; towards the base, close to 77B; immature calyx, close to 185D and margins, close to N200A.

*Inflorescence height*.—About 5.5 cm.

*Inflorescence diameter*.—About 9 cm.

*Flower length (vertical)*.—About 1.4 cm.

*Flower diameter (horizontal)*.—About 8 mm.

*Flower depth (height)*.—About 3.6 cm.

*Petals*.—Arrangement: Labiate; upper lip hooded; lower lip, a single lobe; lips fused lower 70% of total length. Length, upper and lower lips: About 3.3 cm. Width, upper lip: About 2 mm. Width, lower lip: About 8 mm. Shape, upper lip: Lanceolate; apex, narrowly acute. Shape, lower lip: Oblanceolate; apex, acute. Margin, upper and lower lips: Entire; lower petal, slightly undulate. Texture and luster, upper and lower lips, upper surface: Smooth, glabrous; slightly velvety; matte. Texture and luster, upper and lower lips, lower surface: Densely pubescent; velvety; matte. Color, upper lip: When opening and fully opened, upper surface: Close to 77A; color does not change with development. When opening and fully opened, lower surface: Close to N79D; color does not change with development. Color, lower lip: When opening and fully opened, upper surface: Close to 77A; color does not change with development. When opening and fully opened, lower surface: Close to between N79C and N79D; color does not change with development.

*Sepals*.—Quantity and arrangement: Five in a single whorl; lower 87.5% fused into a tubular calyx. Length: About 8 mm. Width: About 1 mm. Apex: Acute. Margin: Free parts, entire. Texture and luster, upper surface: Smooth, glabrous; upper edge of tube, moderately pubescent; matte. Texture and luster, lower surface: Smooth, glabrous; upper edge of tube, moderately pubescent; slightly glossy. Color: When opening, upper and lower surfaces: Close to 185D; apical margins, close to N200A. Fully opened, upper and lower surfaces: Close to between 177D and 181A; apical margins, close to 146A.

*Inflorescence bracts*.—Quantity and arrangement: About 16 at the base of inflorescence. Length: About 2.2 cm. Width: About 1.3 cm. Shape: Ovate. Margin: Entire. Texture, upper surface: Smooth, glabrous; slightly velvety. Texture, lower surface: Densely pubescent. Color: When opening and fully opened, upper surface: Close to 145B to 145C strongly tinged with close to N77A and N77B. When opening and fully opened, lower surface: Close to 146C; towards the base, close to 144A to 144B.

*Reproductive organs*.—Stamens: Quantity per flower: Two. Filament length: About 1.4 cm. Filament color: Close to 77B. Anther length: About 2 mm. Anther shape: Narrowly elliptic; dorsifixed. Anther color: Close to 71A. Pollen amount: Scarce. Pollen color: Close to 8C. Pistils: Quantity per flower: One. Pistil length: About 3.9 cm. Stigma diameter: About 0.5 mm. Stigma shape: Cleft, unequal. Stigma color: Close to N81A. Style length: About 3.75 cm. Style color: Close to N78C to N78D; proximally, close to NN155D. Ovary color: Close to 144B.

*Seed and fruit*.—Seed and fruit production have not been observed on plants of the new *Monarda* to date.

Pathogen & pest resistance: Plants of the new *Monarda* have been observed to be tolerant to Powdery Mildew (*Erysiphe cichoracearum*). Plants of the new *Monarda* have not been observed to be resistant to pests and other pathogens common to *Monarda* plants.

Garden performance: Plants of the new *Monarda* have exhibited good tolerance to rain, wind and high temperatures about 40° C. and to be suitable for USDA Hardiness Zones 5 through 10.

It is claimed:

1. A new and distinct *Monarda* plant named 'MONARD0039' as illustrated and described.

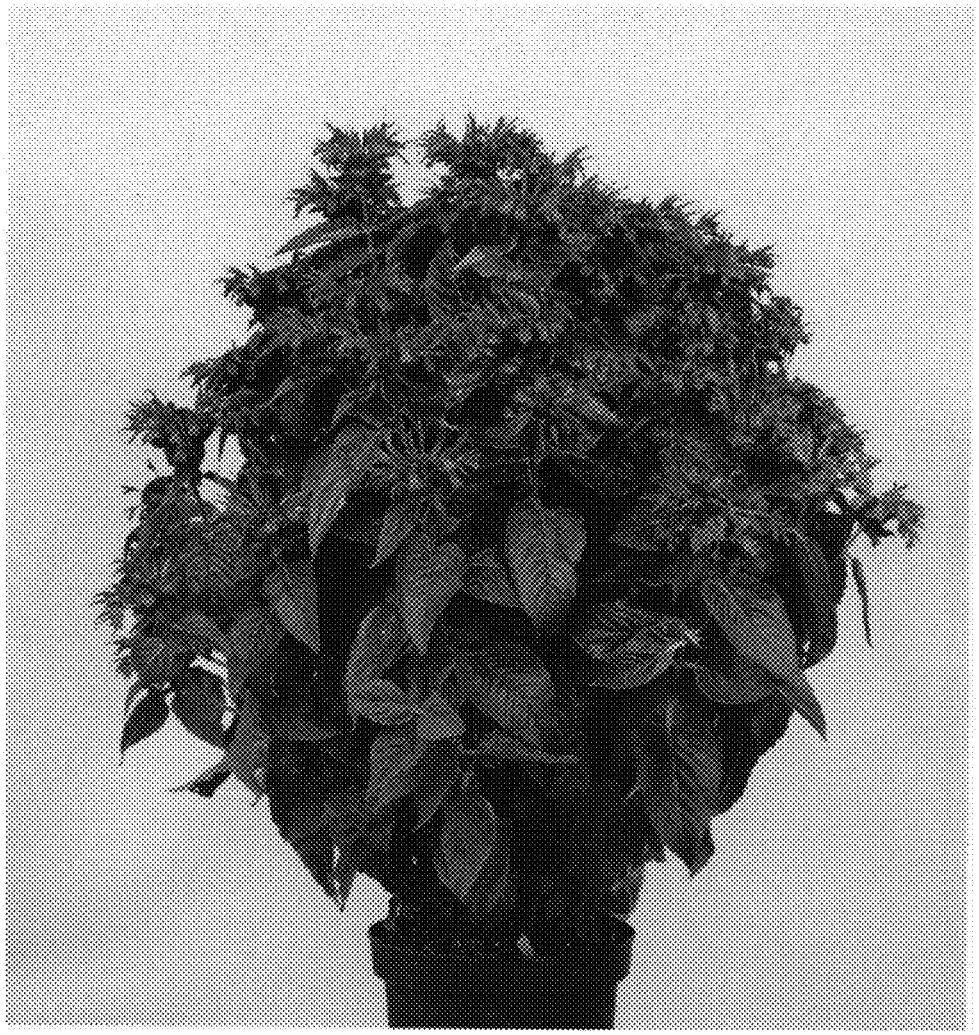

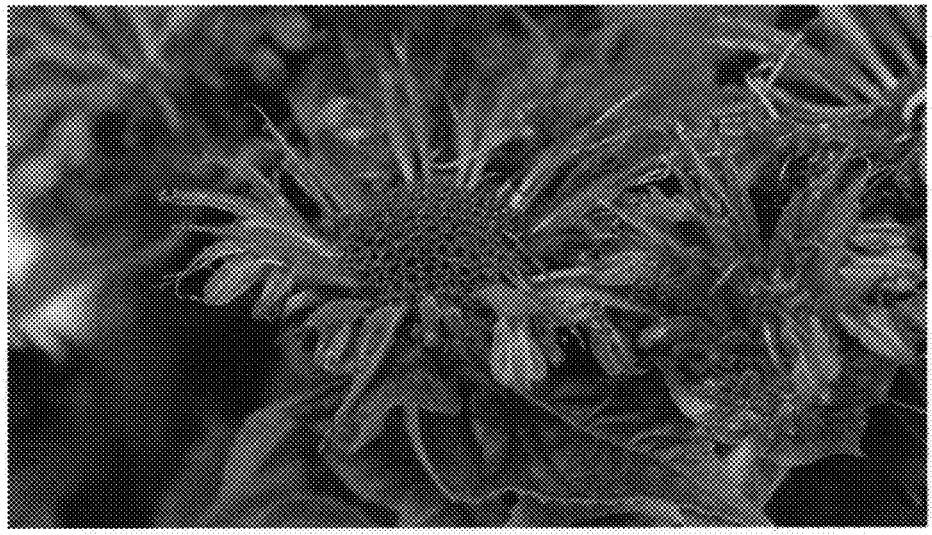
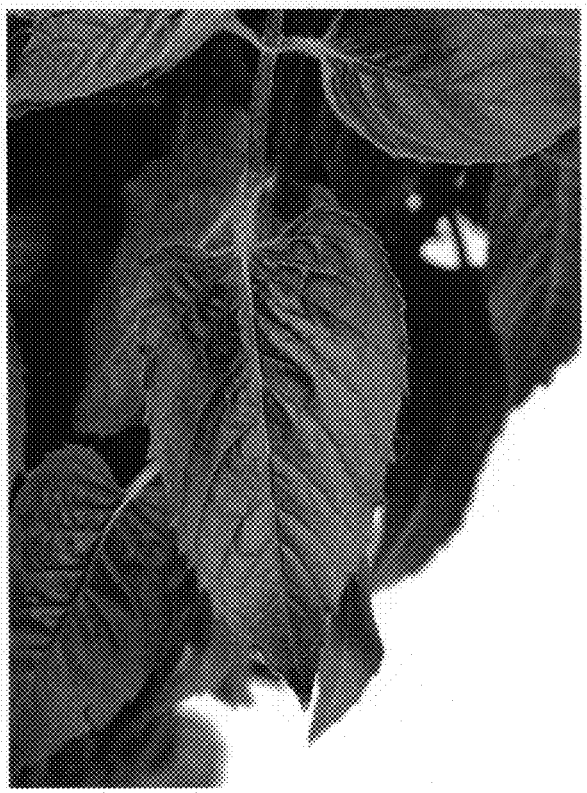

* * * * *